(12) United States Patent
Murata et al.

(10) Patent No.: US 6,878,689 B2
(45) Date of Patent: Apr. 12, 2005

(54) PREVENTIVES OR REMEDIES FOR HEART FAILURE

(75) Inventors: Takahiko Murata, Kyoto (JP); Haruyoshi Ueo, Kyoto (JP); Tadashi Ohyama, Kyoto (JP)

(73) Assignee: Kaken Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 10/312,484

(22) PCT Filed: Jun. 25, 2001

(86) PCT No.: PCT/JP01/05391

§ 371 (c)(1),
(2), (4) Date: Dec. 23, 2002

(87) PCT Pub. No.: WO01/97831

PCT Pub. Date: Dec. 27, 2001

(65) Prior Publication Data

US 2004/0014671 A1 Jan. 22, 2004

(30) Foreign Application Priority Data

Jun. 23, 2000 (JP) .................................. 2000-189175

(51) Int. Cl.[7] .............................. A61K 38/08; A61P 9/04
(52) U.S. Cl. ........................ 514/16; 530/313; 530/329
(58) Field of Search .......................... 514/16; 530/313, 530/329

(56) References Cited

U.S. PATENT DOCUMENTS 5,932,548 A    8/1999  Deghenghi .................. 514/15

FOREIGN PATENT DOCUMENTS

| JP | 10-45619 A | * | 2/1998 |
| JP | 10-045619 A | | 2/1998 |
| WO | WO 98/22124 | | 5/1998 |
| WO | WO 99/08697 A1 | | 2/1999 |
| WO | WO 99/08697 A1 | | 2/1999 |

OTHER PUBLICATIONS

Weekers et al. Pretreatment with Growth Hormone–Releasing Peptide–2 . . . Endocrinology. vol. 141, No. 11, pp. 3993–3999 (Nov. 2000).*
Uchida, Y. et al., Arzneimittel–Forschung, Mar., 1998, 48:219–231.
Ogawa, Hisao, Medicina, May, 1996, 33:934–936.
Yamamoto, Keiji, et al., Medicina, May 1996, 33:847–849.
De Gennaro Colonna, et al., European Journal of Pharmacology 334 (1997), pp. 201–207.
Rossoni, et al., Journal of Cardiovascular Pharmacology 32 (1998), pp. 260–265.
Locatelli, et al., Endocrinology (1999), vol. 140, No. 9, pp. 4024–4031.
Ong, et al., Endocrinology (1998), vol. 139, No. 1, pp. 432–435.
Bodart, et al., Circulation Research 85 (1999), 796–802.
Uchida, et al., Arzneimittel–Forschung (Mar. 1998), vol. 48, No. 3, p. 219–231.
Medicina (May 1996), vol. 33, No. 5, pp. 934–936.
Medicina (May 1996), vol. 33, No. 5, pp. 847–849.

* cited by examiner

*Primary Examiner*—Jeffrey Edwin Russel
(74) *Attorney, Agent, or Firm*—Nixon Peabody LLP

(57) ABSTRACT

Preparations for preventing or treating acute heart failure, chronic heart failure at a phase of acute exacerbation or heart failure at a phase of transition to chronic heart failure, which contain D-alanyl-3-(naphthalen-2-yl)-D-alanyl-L-alanyl-L-tryptophyl-D-phenylalanyl-L-lysinamide and/or salts thereof as an active ingredient.

12 Claims, 4 Drawing Sheets

PREVENTIVES OR REMEDIES FOR HEART FAILURE

CROSS-REFERENCE TO RELATED APPLICATIONS

This application is a 371 National Phase Entry of co-pending International Application No. PCT/JP01/05391, filed Jun. 25, 2001, which designated the U.S. and which claims the benefit under 35U.S.C. §119 of Japanese Application No. 2000-189175, filed Jun. 23, 2000.

TECHNICAL FIELD

This invention relates to preparations for preventing or treating acute heart failure, chronic heart failure at a phase of acute exacerbation or heart failure at a phase of transition to chronic heart failure, that contain as an active ingredient D-alanyl-3-(naphthalen-2-yl)-D-alanyl-L-alanyl-L-tryptophyl-D-phenylalanyl-L-lysinamide (which is a kind of growth hormone releasing peptide and hereunder sometimes termed pralmorelin) and/or salts thereof.

BACKGROUND ART

Among diseases of circulatory organs, a pathologic condition characterized by insufficient blood flow from the ventricle to peripheral organs is called heart failure and classified into acute heart failure and chronic heart failure.

Acute heart failure is defined as a condition of cardiac dysfunction caused by rapid deterioration of the circulation dynamics. Common symptoms include marked dyspnea due to pulmonary congestion or cardiogenic shock due to low cardiac output, expectoration of foamy sputum, oliguria or anuria, cold extremities, lowering of blood pressure, cold sweat and tachycardia (sometimes bradycardia). Unless treated immediately, patients suffering from acute heart failure will soon die. On the other hand, chronic heart failure is an equilibrium state in which compensation mechanisms such as cardiac hypertrophy work because of slow progress of heart failure observed in old myocardial infarction and dilated cardiomyopathy; common symptoms include shortness of breath, fatigability, reduced exercise tolerance, enlargement of the liver and spleen, edema and varicosis of peripheral veins. Therefore, improving the prognosis of life is the ultimate goal of treatment of chronic heart failure and the goals of management are to improve exercise tolerance and the quality of life (QOL).

Thus, acute and chronic heart failures differ in pathological conditions and the object of treatment and it is important to choose the right therapeutic drugs specific to each type of heart failure. For patients with acute heart failure, saving their life is an ultimate goal, cardiotonic preparations are chosen as therapeutics that enhance the reduced myocardial contractility and which can improve the aggravated circulation dynamics. However, if cardiotonic preparations are administered to patients with chronic heart failure who are in stable condition, the already fatigued heart muscle is contracted more by added stimulation with the cardiotonic agent and the condition progresses adversely.

Therapeutics of acute heart failure developed so far are receptor stimulating drugs (e.g. dopamine) and phosphodiesterase (PDE) inhibitors (e.g. amrinone) but their vasodilating action precludes use in hypotensive patients.

Therefore, drugs for acute heart failure are desired that can be used in hypotensive and other patients for whom the application of conventional therapeutics for acute heart failure has not been indicated.

Also desired are pharmaceuticals applicable to the patient during a transition period from completion of treatment for acute heart failure to beginning of chronic heart failure, through which the state of the disease stabilizes slowly.

Reports have been made of the efficacy for heart disease of a growth hormone (hereunder abbreviated as GH), a GH releasing peptide (hereunder abbreviated as GHRP) or a GH secretagogue (hereunder abbreviated as GHS). Pharmacia & Upjohn (WO 9822124) evaluated the efficacy of hexarelin for heart failure in an rat isolated heart(for details, see Berti et al., Eur. J. Pharmacol. 334:201–207, 1997; J. Cardio. Pharmacol. 32:260–265, 1998; and Endocrinology 140:4024–4031, 1999). Eli-Lilly (WO 9908697) evaluated the therapeutic efficacy of GRP-2 (the same molecule as pralmorelin) for chronic heart failure, in particular, congestive heart failure, using rats with hereditary dilated cardiomyopathy.

However, none of these reports include data on the therapeutic efficacy for acute heart failure.

Deghenghi (U.S. Pat. No. 5,932,548) has reported that a specified peptide containing lysine in the sequence binds to the heart and increases its perfusion pressure. According to the more detailed report by Bodart et al. (Circ. Res. 85:796–802, 1999), GHRP elevates the perfusion pressure of the heart and GHRP reduces its contractility instead.

Hence, it has heretofore been unpredictable to use GHRP or GHS in the treatment of acute heart failure.

An object of the invention is to provide a preparation for preventing or treating heart failure that has cardiotonic action based on adequate increase in myocardial contractility and cardiac output. A further object of the invention is to provide a preparation for preventing or treating acute heart failure, chronic heart failure at a phase of acute exacerbation or heart failure at a phase of transition to chronic heart failure. Another object of the invention is to provide a preparation for preventing or treating heart failure that has no side effects including tachycardia, arrhythmia, an increased heart rate and hypotension, in spite of cardiotonic action. A still further object of the invention is to provide a drug for acute heart failure that can be applied to hypotensive and other patients for whom the application of conventional therapeutics for acute heart failure has not been indicated.

DISCLOSURE OF THE INVENTION

As a result of their intensive studies, the present inventors found that among various growth hormone secretagogues, pralmorelin had a significant cardiotonic action based on increased myocardial contractility and cardiac output and thus could solve the aforementioned problems of the prior art; the present invention has been accomplished on the basis of this finding.

The invention provides preparations for preventing or treating acute heart failure, chronic heart failure at a phase of acute exacerbation or heart failure at a phase of transition to chronic heart failure that contain pralmorelin and/or salts thereof as an active ingredient (such preparations are hereunder referred to as "the preparations of the invention" or "the preparations of the subject application").

BEST MODE FOR CARRYING OUT THE INVENTION

Figure 1:
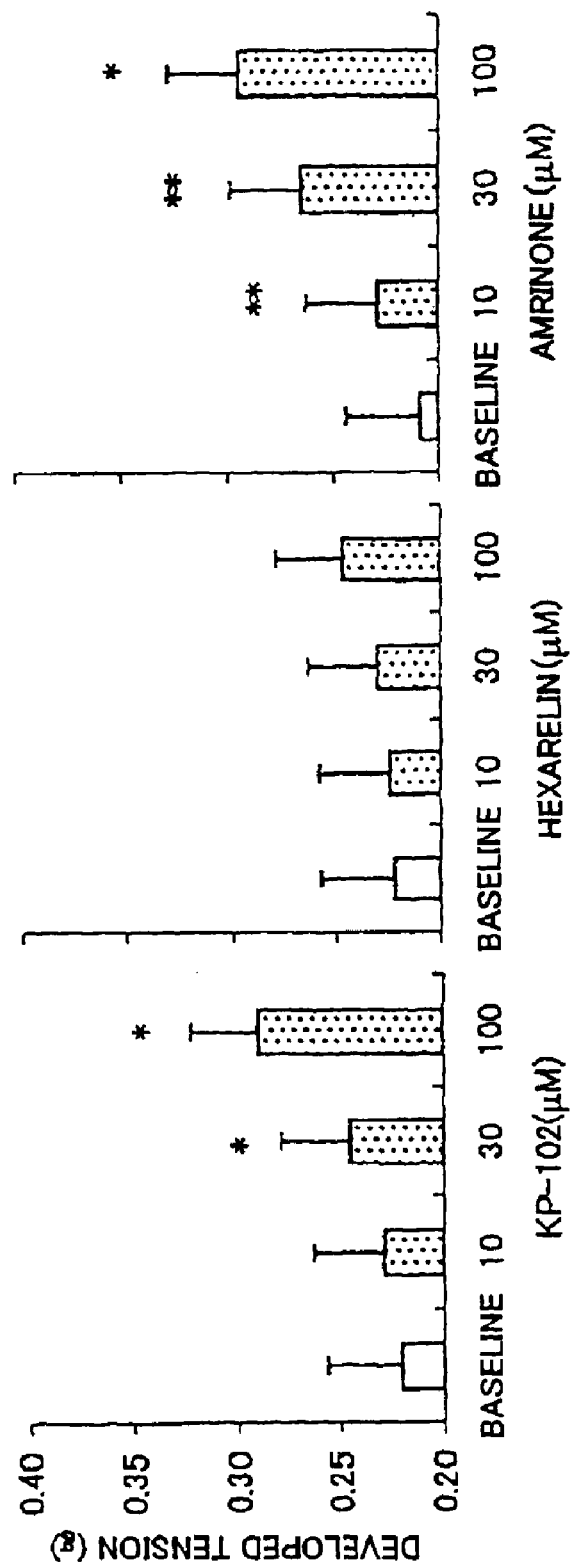
FIG. 1 shows a positive inotropic action of pralmorelin dihydrochloride (hereunder referred to as KP-102), hexarelin and amrinone. The values are expressed by mean ± S.E. (n=5); *: p<0.05; **:p<0.01 vs. baseline value.

The following are preferred embodiments of the invention.

The present invention provides the aforementioned preparation which is characterized in that the active ingredient is an acid addition salt of pralmorelin.

The present invention provides the aforementioned preparation which is characterized in that the active ingredient is pralmorelin dihydrochloride.

The term "acute heart failure" as used herein means a rapid aggravation of circulation dynamics which eventually leads to heart failure and the term "heart failure" means a pathological condition characterized by insufficient blood flow from the ventricle to peripheral organs.

The term "chronic heart failure at a phase of acute exacerbation" means such a condition that chronic heart failure taking a stable time course deteriorates rapidly due to infection or fatigue caused by overwork, manifesting itself as a similar pathological condition to acute heart failure. The term "chronic heart failure" as used herein means a case of heart failure that progresses so slowly that various compensatory mechanisms work to bring the disease into equilibrium.

The term "a phase of transition to chronic heart failure" means a period after the treatment of acute heart failure during which the state of the disease stabilizes slowly until a transition to chronic heart failure occurs. The active ingredient to be used in the preparations of the invention is pralmorelin and/or salts thereof. Pralmorelin can be prepared by known methods such as the one described in JP 7-507039 A (kohyo).

Salts of pralmorelin are acid addition salts. Acid addition salts are used more preferably than the free form in view of drug efficacy. Acids that can form such acid addition salts are those which are capable of forming pharmaceutically acceptable acid addition salts, as selected from, for example, inorganic acids such as hydrochloric acid, sulfuric acid, hydrobromic acid, phosphoric acid and nitric acid, organic acids such as formic acid, acetic acid, propionic acid, succinic acid, glycolic acid, lactic acid, malic acid, tartaric acid, citric acid, maleic acid, phthalic acid, phenylacetic acid, benzoic acid, salicylic acid, methanesulfonic acid, toluenesulfonic acid, benzenesulfonic acid, oxalic acid and trifluoroacetic acid, and amino acids such as aspartic acid and glutamic acid.

Preferred acid addition salts are hydrochlorides and dihydrochlorides are more preferred.

In the preparations of the invention, pralmorelin may be used in combination with two or more acid addition salts thereof.

The pralmorelin and/or salts thereof to be used in the invention can be formulated by known pharmaceutical procedures into ordinary oral preparations or parenteral preparations such as solutions (e.g. injection, nasal drop, syrup and dry syrup), tablets, troches, capsules (e.g. hard, soft and micro-capsules), powders, fine granules, granules, ointments and suppositories, either alone or together with pharmaceutically acceptable carriers, additives, etc.; they can also be formulated into other dosage forms such as drug delivery systems (e.g. sustained-release preparations).

The carriers, additives, etc. that can be used in the preparations of the invention may include the following which are commonly used in the preparation of medicines: aqueous solvents such as physiological saline, water (tap water, distilled water, purified water and water for injection) and Ringer solution; non-aqueous solvents such as oily solvents (e.g. vegetable oils) and water-soluble solvents (e.g. propylene glycol, macrogol, ethanol and glycerin); bases such as cacao butter, polyethylene glycol, microcrystalline wax, white beeswax, liquid paraffin and white petrolatum; excipients such as sucrose, starch, mannitol, sorbitol, lactose, glucose, cellulose, talc, calcium phosphate and calcium carbonate; binders such as cellulose, methylcellulose, hydroxylpropylcellulose, polypropylpyrrolidone, gelatin, gum arabic, polyethylene glycol, sucrose and starch; disintegrants such as starch, carboxymethylcellulose, hydroxypropyl starch, sodium hydrogencarbonate, calcium phosphate, calcium carboxymethylcellulose and calcium citrate; lubricants such as magnesium stearate, talc and sodium lauryl sulfate; flavoring agents such as citric acid, menthol, glycine, sorbitol and orange powder; preservatives and antiseptics such as paraoxybenzoate esters, benzyl alcohol, chlorobutanol and quaternary ammonium salts (e.g. benzalkonium chloride and benzethonium chloride); stabilizers such as albumin, gelatin, sorbitol and mannitol; suspending agents such as methylcellulose, polyvinylpyrrolidone and aluminum stearate; plasticizers such as glycerin and sorbitol; dispersing agents such as hydroxypropylmethyl cellulose; solution adjuvants such as hydrochloric acid; emulsifiers such as sodium monostearate; osmolarity modifiers such as electrolytes (e.g. sodium chloride) and non-electrolytes (e.g. sugar alcohols, sugars and alcohols); and perfumes.

In the case of oral preparations, crystalline cellulose of the type described in JP 10-456194 A (kokai) (AVICEL, the trade name of ASAHI KASEI CORP.) and water-swellable cellulose (e.g. carboxymethylcellulose, calcium carboxymethylcellulose, sodium croscarboxymethylcellulose and hydroxypropylcellulose of low substitution degree) may be incorporated for the purpose of promoting pralmorelin absorption.

The amounts of pralmorelin and/or salts thereof to be contained in the preparations of the invention are not limited to any particular values as long as the desired effects are attained; preferably, they can be contained in the preparations to give concentrations of from about 0.0001 to about 10 w/v %, more preferably from about 0.001 to about 2 w/v %.

The preparations of the subject application are typically administered to mammals including human by suitable means such as intravenous injection (including instillation), oral administration, subcutaneous administration, nasal administration, transpulmonary administration and intraarterial injection. Administration by intravenous injection is preferred.

The dose of administering the preparations of the subject application varies with several factors including the age of the patient, his or her body weight, the severity of the disease and the method of administration. With pralmorelin dihydrochloride taken as an example, the daily dose to an adult by parenteral administration, for example, by intravenous route, is preferably in the range of from about 0.1 to about 1000 μg, more preferably from about 1 to about 100 μg, per kilogram of body weight either in drips or in one to several divided portions; in the case of oral administration, the daily dose is preferably in the range of from about 1 μg to about 10 mg, more preferably from about 10 to about 1000 μg, per kilogram of body weight in several divided portions.

The preventive or therapeutic preparations of the invention can also be used in combination with conventional therapeutics of heart failure such as coronary vasodilators (e.g. nitroglycerin), diuretics (furosemide), existing cardiotonic agents (milrinone) and angiotensin-converting enzyme (ACE) inhibitors (e.g. enalapril oleate) or conventional therapeutics of circulatory diseases such as hypertension (e.g. nicardipine hydrochloride), either simultaneously or at different times.

The preparations of the subject application are useful as preparations for preventing or treating acute heart failure, chronic heart failure at a phase of acute exacerbation or heart failure at a phase of transition to chronic heart failure. In addition, the preparations of the subject application exhibit cardiotonic action based on significant increase in myocardial contractility and cardiac output, so they are particularly effective when used in the prevention or treatment of acute heart failure.

The following preparation and test examples are provided for specifically describing the present invention but are in no way to be taken as limiting.

PREPARATION EXAMPLES

Preparation Example 1

Pralmorelin dihydrochloride was dissolved in physiological saline to prepare 0.01 w/v %, 0.02 w/v % and 0.1 w/v % solutions.

Preparation Example 2

Gelatin capsules were filled with 11 mg of pralmorelin dihydrochloride and 189 mg of lactose to prepare capsules.

Test Examples

The fact that the pralmorelin used in the preparations of the invention has outstanding cardiotonic action on heart failure is demonstrated by test examples.

[Test Example 1] Myocardial Contractility Enhancing Action of Pralmorelin in the Papillary Muscle of Guinea-Pig The direct effect of pralmorelin on myocardial contractility was evaluated using the isolated cardiac muscle of guinea-pigs according to the standard method for evaluating myocardial contractility.

1. Materials and Experimental Method
1) Animal Used

Male Hartley guinea-pigs (body weight, 301–350 g; Japan SLC) were purchased. The animals were accommodated to an environment at a temperature of 23±2° C. and a humidity of 55±15% under 12-hr light/dark cycles while they were allowed to eat and drink water ad libitum until they weighed 360–480 g. Each test substance was tested on a group of five animals.

2) Reagents Used

The test substances were pralmorelin dihydrochloride (KP-102), representatives of growth hormone secretagogues such as hexarelin, ghrelin and ibutamorelin methanesulfonate (the last being hereunder referred to as MK-0677) (which were prepared by the method described in JP 6-263737 A (kokai)), as well as a recombinant human growth hormone (Sumitomo Pharmaceutical) and amrinone (Sigma) which is a known therapeutic of acute heart failure. KP-102, hexarelin and MK-0677 were dissolved in distilled water. Ghrelin was dissolved in physiological saline. Amrinone was first dissolved in dimethyl sulfoxide and then diluted with physiological saline. The growth hormone was dissolved in a dedicated solubilizer (0.3 w/v % metacresol and 3.9 w/v % D-mannitol). None of the test substance solutions should be added in an amount exceeding 1 w/v %. All reagents other than the test substances were guaranteed products of Nacalai Tesque.

3) Preparing Specimens of the Isolated Papillary Muscle

The guinea-pigs were stunned with a blow to the back of their head; thereafter, the carotid artery was incised and the animals were exsanguinated to death. The chest was opened, the blood vessels in the upper part of the heart were cut and the heart was removed. The heart was immediately transferred into a Krebs-Henseleit (K-H) nutrient solution (NaCl, 118.0 mM; KCl, 4.7 mM; $CaCl_2 \cdot 2H_2O$, 1.0 mM; $KH_2PO_4$, 1.2 mM; $MgSO_4 \cdot 7H_2O$, 1.2 mM; $NaHCO_3$, 25.0 mM; glucose, 11.0 mM) that had been fully aerated with 95% $O_2$-5% $CO_2$. The heart was fixed on a rubber-lined Petri dish with needles such that its front face was seen. The ventricular wall of the upper right ventricle (toward the atrium) was excised transversely along the atrium, then excised longitudinally along the interventricular septum so that the ventricular wall was opened to expose the right ventricular papillary muscle. Subsequently, the entire surface of the left ventricle was cut open from the aorta (down) to the apex and the anterior wall of the left ventricle was opened wide, to both right and left, and fixed to expose the papillary muscle of the left ventricle. The tricupsid or mitral valve was cut off from the ventricle and the papillary muscle was cut off at the base to prepare a specimen of papillary muscle. The base of the specimen was fixed to field stimulating electrodes in an organ bath filled with 15 mL of the nutrient solution. The tendinous cord adhering to the valve was tied up with a thread and connected to an FD pickup (TB-612T, Nihon Kohden). A resting tension of 0.5 g was loaded and the papillary muscle was driven with an electric stimulator (SEN-3201, Nihon Kohden) at a frequency of 1 Hz by pulses of 20-ms duration and at a voltage intensity about 1.2 times the threshold. After an equilibration period of about 1 hr, KP-102, hexarelin and amrinone were each applied cumulatively up to amounts of 10, 30 and 100 μM. After examination of the changes in inotropic action due to the application of the test substances, 12.5 mM of $CaCl_2$ was added and the maximum tension that was developed by each specimen was obtained. The developed tension was recorded with a multi-purpose preamplifier (RMP-6008, Nihon Kohden) and a recorder (WT-647G, Nihon Kohden).

4) Methods of Data Display and Analysis

Each result was expressed by mean ± standard error. Statistical significances of the positive inotropic action of each test substance were processed by a paired t-test in comparison with the initial value (indicated as "BASELINE" in FIG. 1) and differences were considered significant at the level of $p<0.05$.

2. Results

Before the application of each test substance, no significant difference was found between the papillary muscle specimens of any two animal groups in terms of the developed tension and the maximum developed tension.

The groups applied with the recombinant human growth hormone (0.2 IU/mL), ghrelin (1 μM) and MK-0677 (100 μM) showed no changes in the developed tension.

In the other groups, the tension development increased in a concentration-dependent manner from 10 to 100 μM as shown in FIG. 1. However, the efficacy differed among the test substances; KP-102 showed a significant effect over the baseline value and this was almost comparable to the effect of amrinone; on the other hand, the effect of hexarelin was very weak and by no means significant over the baseline value.

[Test Example 2] Effects of Intravenously Administered Pralmorelin on the Cardiac Function of Rabbit The effects of pralmorelin on cardiac function were evaluated by measuring various parameters [blood pressure, heart rate, systolic left ventricular pressure (LVPsys), and maximal positive dP/dt (+dP/dtmax) obtained by differentiating the waveform of left ventricular pressure (LVP)]. The value of the maximal positive dP/dt for the left ventricular pressure (+dP/dtmax) is particularly important to determine if the cardiotonic action is sufficient to treat acute heart failure.

1. Test Substance and Reagent

1) Test Substance

Pralmorelin dihydrochloride (hereunder referred to as KP-102) (prepared by the method described in WO 9304081) was dissolved in distilled water for injection to prepare a 1.5 mg/mL solution.

2) Control

JP distilled water for injection (Otsuka Pharmaceutical Co., Ltd.) was used.

3) Reagent

For anesthetizing animals, sodium pentobarbital (Nacalai Tesque) was dissolved in physiological saline (Otsuka Pharmaceutical Co., Ltd.) to give a concentration of 15 mg/mL.

2. Animal Used and Keeping Conditions

Male NZW-strain rabbits (Kitayama Labes) weighing about 2 kg were used in the experiment. After arrival, the animals were allowed to eat a solid meal (Labo R Stock, Oriental Yeast Co., Ltd.) and drink water in a room at a temperature of 20±2° C. and at a humidity of 55±15% under 12-hr light/ dark cycles (from 7:00 to 19:00); the animals were kept under these conditions for at least 6 days before use.

3. Test Method

1) Measuring the Cardiac Function of Anesthetized Open-Chest Rabbit

Rabbits were anesthetized by administering 30 mg/kg of sodium pentobarbital into the auricular vein at a slow speed with attention to their breathing. The animals were then fixed in supine position and an endotracheal cannula was inserted. Under artificial respiration (tidal volume, 25 mL/breath; ventilation frequency, 45 breaths/min: SN-480-7 of Shinano Seisakusyo), the chest of each animal was opened by midline incision and the pericardium was incised to expose the heart. The left ventricular pressure (LVP) was measured with a pressure transducer (TP-300T, Nihon Kohden) and a pressure amplifier (AG-610G, Nihon Kohden) as a cannula with syringe was inserted from the cardiac apex into the left ventricle. The waveform of LVP was differentiated with a differentiator unit (ED-601, Nihon Kohden) to determine the maximal positive dP/dt(+dP/dtmax), which was used as an index for cardiac contractility. Blood pressure was measured with a pressure amplifier (AP-610G, Nihon Kohden) via a pressure transducer (TP-300T, Nihon Kohden) connected to a cannula inserted into the left femoral artery. Heart rate was measured with a cardiotachometer (AT-601G, Nihon Kohden) that was driven by counting the pulse waves of LVP. The parameters mentioned above were recorded on a recorder (TA-11, Gould). A cannula was inserted into the left femoral vein so as to assist in the administration of the test substance. The rectum temperature of each animal was controlled at 39° C.

with a body temperature controller (TK-43, Asahi Denshi). The anesthetic was added as required but additional anesthetization should be avoided during the measurements.

2) Groups

Test was conducted in the following two groups.

| | |
|---|---|
| Control group (administered distilled water) | n = 4 |
| KP-102 group (administered 300 µg/kg) | n = 4 |

(Note: Nine rabbits were used in the experiment but one of the rabbits in the control group was excluded because all parameters suddenly began to change greatly in 3 minutes after the administration of the vehicle. Hence, a total of eight rabbits in two groups, each consisting of four, were subjected to the test.)

3) Test Protocol

After each parameter stabilized, distilled water (0.2 mL/kg) was administered over one minute with an infusion pump (FP-W-100, Toyo Sangyo K.K.) and observations were made for 5 minutes after the administration to see whether the vehicle would have no effect. About 5 minutes after the administration of distilled water, the test substance was administered with an infusion pump in a volume of 0.2 mL/kg over one minute according to the grouping method specified above. Each hemodynamic parameter was measured both before administration and 1, 3, 5, 10, 15, 20 and 25 minutes after administration and the percent changes from the basal values were calculated. In some animals, measurement was conducted until 40 minutes after the administration of the test substance.

4. Statistical Analysis

The results were each expressed by mean ± standard deviation. Any difference between groups was tested by repeated measures ANOVA (analysis of variance); The significance level was set at 5%.

5. Results

1) Baseline Values in Each Group

The baseline values of parameters (body weight, mean blood pressure, heart rate, LVPsys and +dP/dtmax) in each group are listed in Table 1.

TABLE 1

| Parameter | Control (n = 4) | KP-102 (n = 4) |
|---|---|---|
| Body weight (kg) | 2.14 ± 0.10 | 2.17 ± 0.07 |
| Mean blood pressure (mmHg) | 68 ± 16 | 77 ± 6 |
| Heart rate (beats/min) | 299 ± 13 | 321 ± 5* |
| Systolic left ventricular pressure (mmHg) | 105 ± 22 | 120 ± 12 |
| +dP/dtmax (mmHg/sec) | 4599 ± 1333 | 5770 ± 1477 |

Mean ± standard deviation; *$p < 0.05$

In the adopted animal groups, none of the parameters of measurement were affected by the administration of distilled water as the vehicle.

No significant inter-group difference was observed in the baseline values of body weight, mean blood pressure, LVPsys and +dP/dtmax; however, a significant difference was observed in heart rate (299±13 in the control group and 321±5 in KP-102 group). This was a mere deviation in the normal range and the difference, with its cause being unknown, was so slight that there would be no influence on the evaluation of the cardiac contractility.

Figure 2:
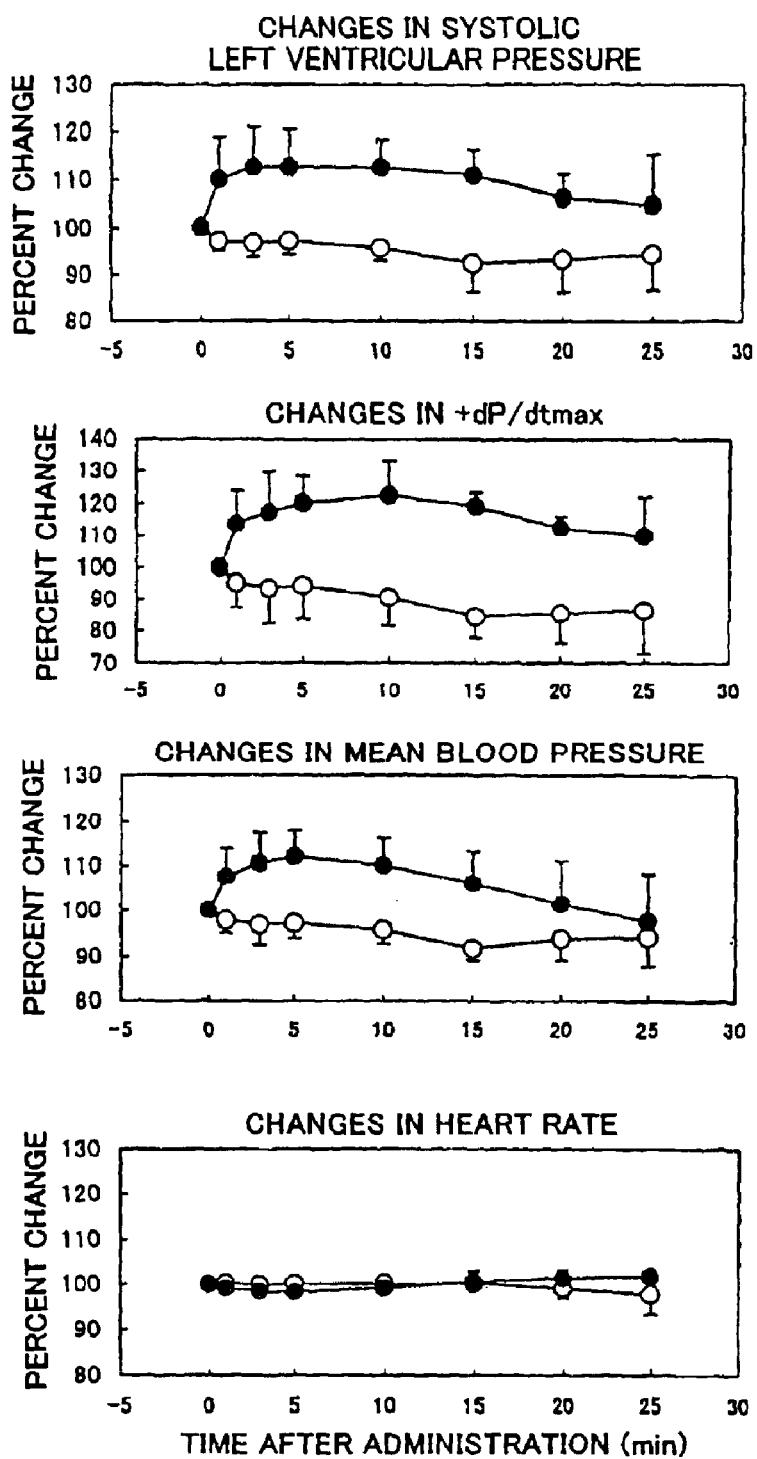
FIG. 2 shows effects of KP-102 on the systolic left ventricular pressure, +dP/dtmax, mean blood pressure and heart rate in anesthetized open-chest rabbits. The values are expressed by mean ± standard deviation (n=4).

2) Effects of Pralmorelin on LVPsys, +dP/dtmax, Mean Blood Pressure and Heart Rate (FIG. 2)

LVPsys. +dP/dtmax and Mean Blood Pressure

In the control group, LVPsys, +dP/dtmax and mean blood pressure were found to have a tendency to decrease spontaneously in only 15 minutes after the administration.

In all four cases of the group intravenously administered 300 µg/kg of KP-102, LVPsys and +dP/dtmax increased, showing significant changes in comparison with the control group ($p < 0.01$). This cardiotonic action was observed beginning one minute after the administration, drew a curve peaking in the period of 5–10 minutes and did not completely return to the baseline value even after 25 minutes. Maximum increases in LVPsys and +dP/dtmax were 13% and 22%, respectively, of the baseline values. In one case after the administration of KP-102 and extended monitoring, the baseline values were found to be restored within 40 minutes.

In the group administered KP-102, the increase in LVPsys was accompanied by a significant rise of blood pressure ($p < 0.05$) but the change was transient and the baseline value was practically restored in 25 minutes after the administration.

Heart Rate

In the control group, the heart rate did not change until 15 minutes after the administration and then it dropped by 1% in 20 minutes and by 2% in 25 minutes. In the group administered KP-102, the heart rate dropped by 2% in 3 minutes after the administration, then returned to the baseline value, increased by 1% in 15 minutes after the administration and by 2% in 25 minutes; thus the variation pattern was obviously different from that in the control group. Therefore, an interaction was observed between the control group and the group administered KP-102 ($p < 0.01$). However, the variation in heart rate was as small as 2% in both the control group and the group administered KP-102 and it was concluded that the heart rate would be little affected by KP-102.

[Test Example 3] Effect of Intravenously Administered Pralmorelin on the Cardiac Function of Dog with a Model of Anterior Descending Coronary Artery Occlusion Using a dog model of acute contractile dysfunction caused by occlusion of the anterior descending coronary artery, the inventors studied the cardiotonic action of pralmorelin.

The action of pralmorelin on the cardiac dysfunction deteriorated by occlusion of the coronary artery was evaluated by various hemodynamic parameters, cardiac output (CO), stroke volume (SV), maximal positive dP/dt of left ventricular pressure (+dP/dtmax), ejection fraction (EF), mean blood pressure (MBP), heart rate (HR), total peripheral resistance (TPR) and double product (RPP) as an index of myocardial oxygen consumption.

1. Test Materials and Method
1) Test Substance and Reagents
(1) Control

JP distilled water for injection (hereunder referred to as distilled water, Otsuka Pharmaceutical Co., Ltd.).

(2) Test Substance

Pralmorelin dihydrochloride (hereunder referred to as KP-102) (prepared by the method described in WO 9304081) was dissolved in distilled water to prepare a 0.5 mg/mL solution.

(3) Reagents

Sodium pentobarbital (hereunder referred to as "pentobarbital", Nacalai Tesque) was dissolved in physiological saline (Otsuka Pharmaceutical Co., Ltd.) to prepare a 30 mg/mL solution for anesthesia. In order to avoid irritation on the trachea, xylocaine (xylocaine spray, Astra Zeneca) was applied several times to an endotracheal cannula.

2) Animal Used

In the experiment, adult beagles of either sex (weighing 9–11 kg) purchased from Nihon Nosan Kogyo K.K. (Kanagawa, Japan) were used. After arrival, the animals were allowed to eat a solid meal (CD-5, CLEA Japan, Inc. or Labo D Stock, Nark Corp.) and drink water in a room at a temperature of 20±2° C. and at a humidity of 55±15% under illumination for 12 hours a day (from 7:00 to 19:00); the animals were kept under these conditions for at least one week before use.

3) Method of Measurement

Anesthesia was introduced by intravenous administration of pentobarbital (30 mg/kg) and in order to maintain anesthesia, pentobarbital (5–6 mg/kg/hr) was injected continuously by means of an infusion pump (FP-W-100, Toyo Sangyo) through a polyethylene cannula retained in the right cephalic vein. The endotracheal cannula was inserted and the chest was opened at the left fourth intercostal space under artificial respiration in a tidal volume of 20 mL/kg at a rate of 18 breaths/min with an artificial respirator (SN-480-3 of Shinano Seisakusho). The left anterior descending coronary artery was carefully detached from the site of origin over a length of 1–2 cm and an occluding thread was passed through.

The chest was opened at the left fifth intercostal space and a 5-segment conductance catheter (CCS-108-DA, Unique Medical) was inserted from the cardiac apex so that all electrodes would be placed in the left ventricle. A catheter equipped with a 5 Fr microtip pressure transducer (pressure transducer catheter, Model MPC-500, MILLAR) was inserted into the left ventricle through the left carotid artery. The conductance catheter and the pressure transducer catheter inserted into the left ventricle were connected to a built-in amplifier in a ventricular volume-measuring instrument (Integral 3; VPR-1002, Unique Medical) and the changes in the left ventricular pressure (LVP) and the volume of the left ventricle were measured simultaneously. To determine the mean blood pressure (MBP), blood pressure was measured via a blood pressure amplifier (AP641G, Nihon Kohden) from the 5 Fr pressure transducer catheter inserted into the left femoral artery. Heart rate (HR) was measured with a cardiotachometer (AT-601G, Nihon Kohden) from the pulse waves of blood pressure.

The chest was opened again at the fourth intercostal space and in order to measure the cardiac output (CO(EMF)) (CO as determined by an electromagnetic blood flowmeter based method), a probe connected to an electromagnetic blood flowmeter (MFV-2100, Nihon Kohden) was fitted at the site of origin of the aorta. A spiral electrode was put in the ischemic region that occurred due to the occlusion of coronary artery and a surface electrocardiogram was recorded. A Doppler probe was fitted on the left anterior descending coronary artery and the blood flow was determined with a Doppler blood flowmeter (PD-20, Crystal Biotech). The anterior descending coronary artery was occluded with pulling up the occluding thread over a period of about 5 minutes. Complete occlusion of the blood vessel was confirmed by the change in the surface electrocardiogram and the disappearance of the Doppler sound.

In order to calculate the ventricular volume from the voltage between segments as measured with the conductance catheter, blood resistivity ($\rho$) was measured before the occlusion of the coronary artery. After the end of measuring the drug-induced effect, saturated saline was injected through the right femoral vein to determine the volume error (Vp) due to an extraventricular leakage current. The values of $\rho$ and Vp were input to the analytical software package (Integral 3 ver.2.42, Unique Medical) which was an accessory to the ventricular volume-measuring instrument. From the changes in LVP, +dP/dtmax, –dP/dtmax, systolic left ventricular pressure (LVPsys) and left ventricular end-systolic pressure (LVEDP) were calculated, and from the changes in ventricular volume, stroke volume (SV) and cardiac output (CO) were calculated. The hemodynamic parameters were recorded on a recorder (TA-11, Gould). Total peripheral resistance (TPR) and the double product (RPP) as an index of myocardial oxygen consumption were calculated by the following formulae:

$$TPR=MBP/CO$$

$$RPP=MBP \times HR$$

Throughout the experiment, the body temperature of the animals was controlled at 37° C. by means of body temperature controllers (TK43 of Asahi Denshi Kogyo and KN-474 of Natsume Seisakusho). No additional anesthesia was injected during the measurements.

4) Groups

Test was conducted in the following two groups.

| | |
|---|---|
| Control group (administered distilled water after the occlusion of the coronary artery): | n = 4 |
| KP-102 group (administered 100 μg/kg of KP-102 after the occlusion of the coronary artery) | n = 5 |

5) Experimental Protocol

Following the occlusion of the anterior descending coronary artery, +dP/dtmax and CO dropped. After these and other hemodynamic parameters stabilized, the test substance (0.2 mL/kg/min) was injected into the left femoral vein over one minute with an infusion pump (FP-W-100, Toyo Sangyo). Immediately thereafter, distilled water (0.2 mL/kg/min) was injected for an additional period of about 30 seconds. Each circulation parameter was measured both before administration and 1, 3, 5, 10, 15, 20, 25, 30, 40, 50 and 60 minutes after the administration; the effects of occlusion were evaluated in terms of the percent change relative to the pre-occlusion values, and the action of pralmorelin was evaluated in terms of the percent change relative to the baseline values before the administration.

6) Statistical Analysis

The results were expressed by mean ± standard deviation.

Any inter-group difference in the values of individual parameters before and after occlusion of the coronary artery was checked by an unpaired t-test. Any intra-group difference in the values of individual parameters before and after occlusion of the coronary artery was checked by a paired t-test.

Any inter-group difference in the values of individual parameters after the administration of the test substance was tested by repeated measures ANOVA (analysis of variance). The significance level was set at 5%. Since no difference was found between the change of CO(EMF) and that of CO, analysis was performed on CO (as determined from the change in ventricular volume)

2. Results

1) Values in Each Group Before Administration of the Test Substance

Prior to the occlusion of the coronary artery, there was no significant difference in body weight between the control group and the KP-102 group (9.93±0.56 kg in the control group and 9.67±0.20 kg in the KP-102 group); in addition, none of the hemodynamic parameters had any significant difference between the two groups (Table 2).

We next investigated the effects of occlusion of the coronary artery before the test substance was administered to each group.

Within 20 minutes after the occlusion of the anterior descending coronary artery, post-occlusion premature contraction occurred in all animals. Thereafter the frequency had a tendency to decline gradually; in 30–80 minutes after the occlusion, the hemodynamic parameters stabilized (Table 2).

As a result, it was found that the occlusion of the coronary artery caused CO to drop by 15% (18% in the control group and 14% in the KP-102 group), +dP/dtmax by 7% (control, 5.4%; KP-102, 8.7%) and EF (ejection fraction) by 29% (control, 31%; KP-102, 24%), as compared to the pre-occlusion values (p<0.05); the occlusion also caused significant drops (p<0.05) in SV and –dP/dtmax in both groups; however, no significant difference was found in MBP, LVEDP, HR and TPR as compared with the pre-occlusion values. There were no significant inter-group differences in the hemodynamic parameters after occlusion of the coronary artery.

TABLE 2

Values of cardiohemodynamic parameters in anesthetized open-chest dogs as measured both before and after occlusion of the coronary artery

| Parameters | Control group (n = 4) | | KP-102 group (n = 5) | |
| --- | --- | --- | --- | --- |
| | Baseline | After occlusion | Baseline | After occlusion |
| MBP (mmHg) | 98.9 ± 18.6 | 97.1 ± 20.4 | 96.5 ± 11.1 | 94.1 ± 13.5 |
| HR (beats/min) | 132.3 ± 15.3 | 138.5 ± 19.1 | 142.6 ± 13.8 | 142.8 ± 13.1 |
| CO (mL/min) | 591.0 ± 182.8 | 500.8 ± 221.7* | 570.0 ± 165.1 | 483.4 ± 91.2* |
| SV (mL/beats) | 4.43 ± 0.95 | 3.55 ± 1.18** | 3.96 ± 0.76 | 3.34 ± 0.36* |
| EF (%) | 77.1 ± 7.8 | 52.2 ± 6.7* | 66.6 ± 21.2 | 52.1 ± 14.6* |
| LVPsys (mmHg) | 122.0 ± 16.0 | 116.0 ± 16.5** | 126.6 ± 14.1 | 118.7 ± 17.3 |
| LVEDP (mmHg) | 5.5 ± 1.4 | 6.0 ± 1.2 | 8.14 ± 4.7 | 9.2 ± 5.0 |
| +dP/dtmax (mmHg/sec) | 2413.3 ± 414.5 | 2284.8 ± 405.6** | 2473.8 ± 592.2 | 2255.8 ± 575.2* |
| –dP/dtmax (mmHg/sec) | 2871.0 ± 320.0 | 2507.3 ± 465.9* | 3059.2 ± 689.2 | 2459.4 ± 536.9* |
| RPP (mmHg · beats/min) | 13231 ± 4002 | 13710 ± 4952 | 13856 ± 2874 | 13559 ± 3250 |
| TPR (mmHg/L/min) | 174.5 ± 39.3 | 215.1 ± 74.5 | 174.9 ± 27.0 | 195.8 ± 10.8 |

Each value represents mean ± standard deviation.
* and ** indicate significant differences from the baseline in the same group at $p < 0.05$ and $p < 0.01$, respectively (Student's paired t-test). No significant difference was observed between control group and KP-102 group at corresponding time points.

Figure 3:
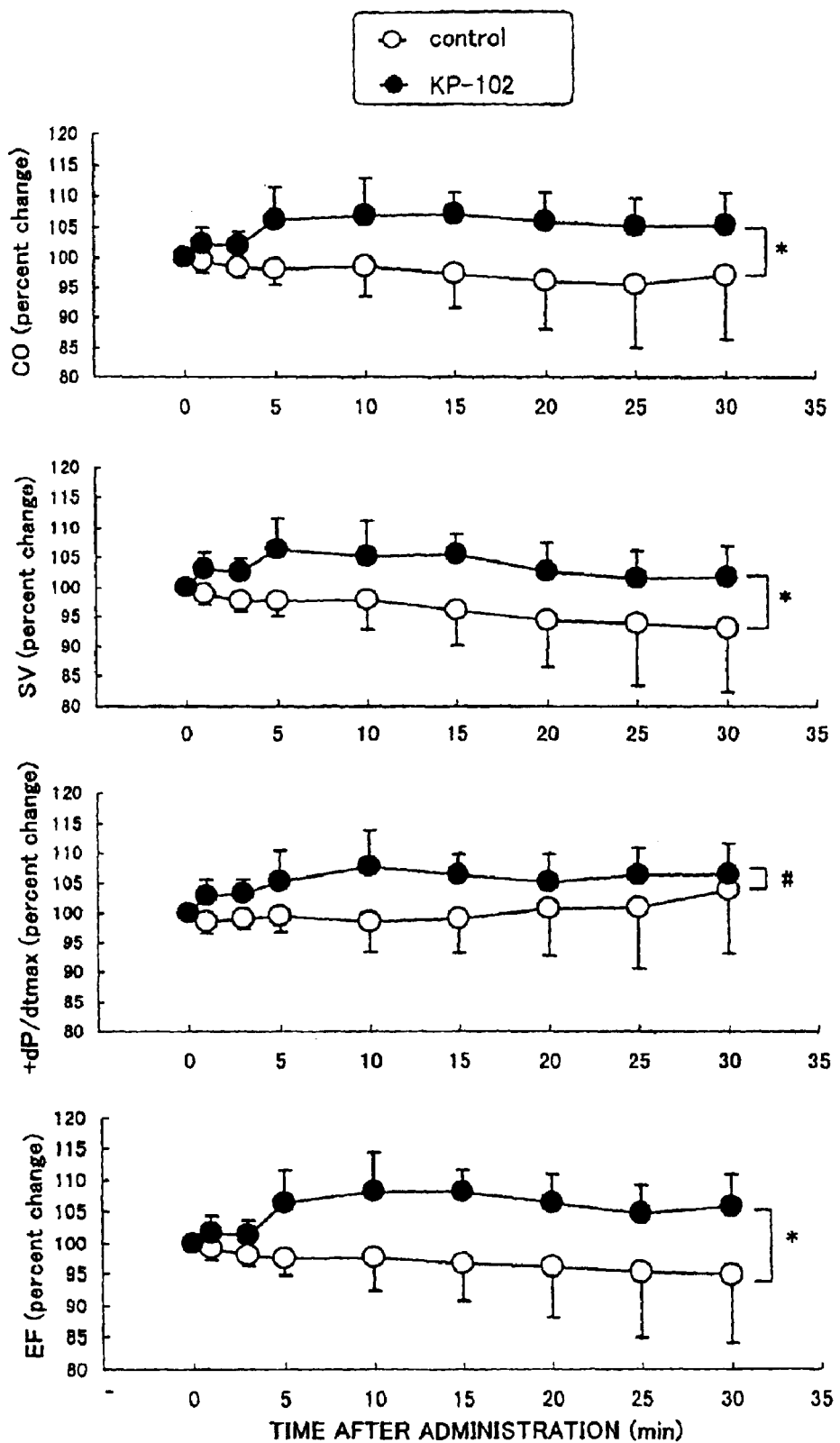
FIG. 3 shows an ameliorating effect of KP-102 on the cardiac output (CO), stroke volume (SV), maximum left ventricular pressure +dP/dt (+dP/dtmax) and ejection fraction (EF) in dogs with occluded anterior descending coronary artery. The values, being the percentage of the value after stabilization of the state of the disease relative to the value just before administration of the drug, are expressed by mean ± standard deviation; differences were considered significant at the levels of *: p<0.05 (compared by repeated measures analysis of variance with the value in the control group for the lapse of 30 minutes from the administration of the drug) and #: p<0.05 (compared by repeated measures analysis of variance with the value in the control group for the lapse of 20 minutes from the administration of the drug).
Figure 4:
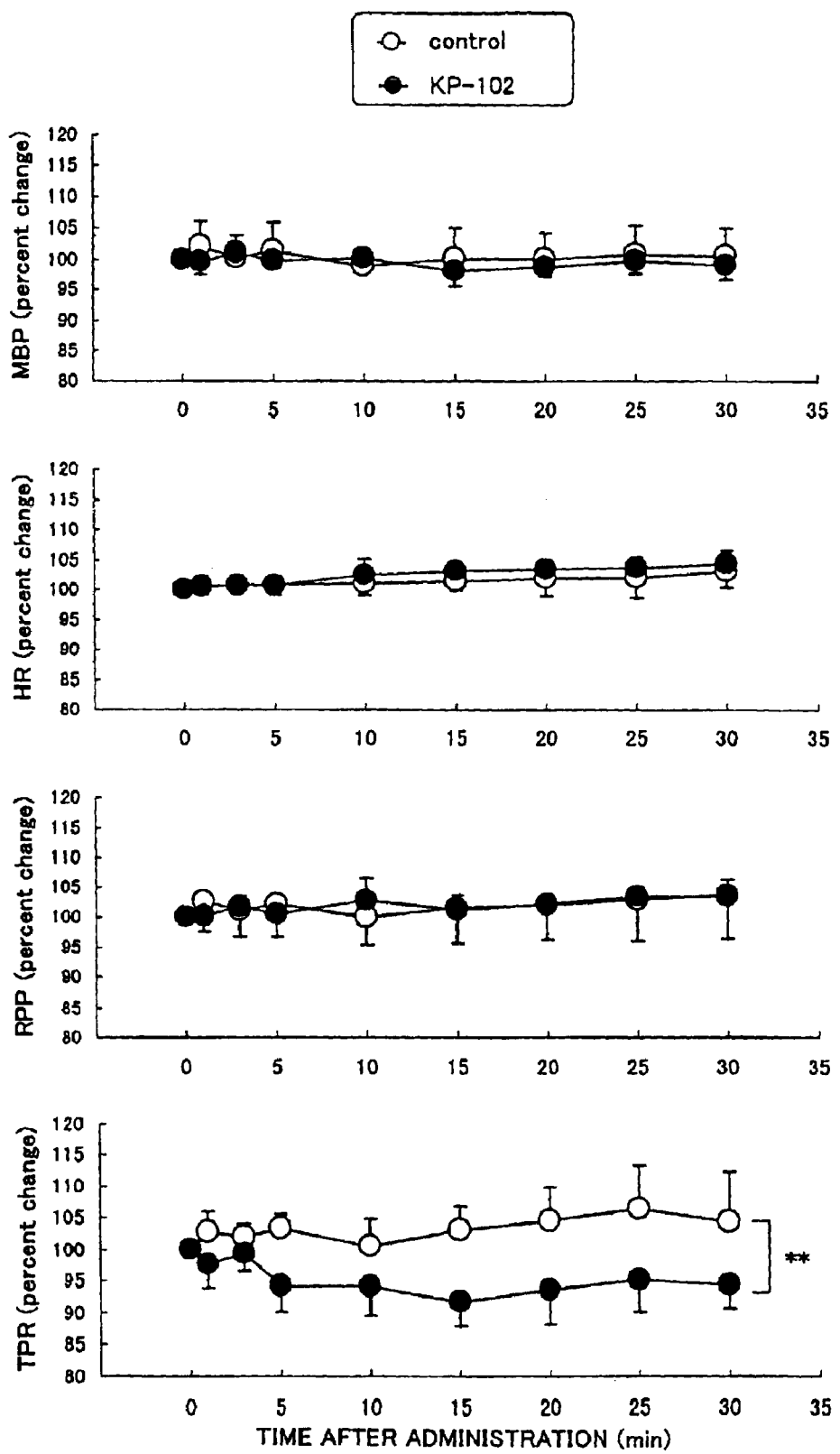
FIG. 4 shows the effects of KP-102 on the mean blood pressure (MBP), heart rate (HR), double product (RPP) and total peripheral resistance (TPR) in dogs with occluded anterior descending coronary artery. The values, being the percentage of the value after stabilization of the state of the disease relative to the value just before administration of the drug, are expressed by mean ± standard deviation; differences were considered significant at the level of **: p<0.01 (compared by repeated measures analysis of variance with the value in the control group for the lapse of 30 minutes from the administration of the drug).

2) Effects of Pralmorelin on Cardiovascular System(FIGS. 3 and 4)

KP-102 and distilled water were administered to each of the animal groups of which cardiac functions were deteriorated by the occlusion of the coronary artery. The resulting effects on cardiovascular system were shown in FIGS. 3 and 4 as percentage changes from the baseline values.

Action on CO and SV

In the control group, both SV and CO hardly changed after the administration of distilled water. In the group administered KP-102, CO increased by a maximum of 7% in 10 minutes after the administration and SV increased by 5% in 5 minutes after the administration. The changes in both CO and SV were significant in comparison with those of control group (p<0.05).

Action on +dP/dtmax and –dP/dtmax

In the control group, neither +dP/dtmax nor –dP/dtmax changed. In the group administered KP-102,–dP/dtmax showed no significant change in comparison with that of the control group. But, +dP/dtmax increased by 7% in 10 minutes after the administration and the changes for the first 20 minutes period had significant differences from the control group(p<0.05).

Action on EF The control group maintained the lower level resulting from the occlusion of the coronary artery. In contrast, the KP-102 group showed increasing action with a maximal increase of 10% in 10 minutes, which was a significant difference from the control group.

Action on MBP. HR and RPP

Neither of MBP and HR changed in the control group and the KP-102 group. Neither group experienced a change in RPP which was an index of myocardial oxygen consumption and there was no inter-group difference in RPP.

Action on LVPsys and LVEDP

Neither of the control and KP-102 groups showed changes in LVPsys and LVEDP and there was no inter-group difference in those parameters.

Action on TPR

In the control group, TPR which increased as the result of occlusion of the coronary artery remained at the higher level. In contrast, in the group administered KP-102, TPR dropped following the administration. Thus, a significant difference was observed between the two groups ($p<0.05$).

3. Discussion

In the model of acute dysfunction in cardiac contraction, KP-102 increased the cardiac output (CO), stroke volume (SV) and +dP/dtmax without changing the mean blood pressure (MBP), heart rate (HR) and the double product (RPP); hence, KP-102 could enhance the cardiac function that had been deteriorated by the occlusion of the coronary artery. Further, KP-102 significantly increased the ejection fraction (EF) that had been lowered by the occlusion of the coronary artery. Ejection fraction (EF) can be measured non-invasively in echocardiography, so it is frequently used in clinical settings as a parameter for evaluating cardiac contractility. From the studies made so far, it is held desirable for the treatment of heart failure to avoid varying both the heart rate (HR) and the double product (RPP) which is an index for myocardial oxygen consumption. Hence, the foregoing findings on KP-102 support its potential clinical efficacy.

Present studiies verified that KP-102 is effective not only for the cardiac function of normal animals but also for the deteriorated cardiac function of animals with acute contractile dysfunction by exhibiting cardiotonic action based on marked increases in myocardial contractile force and cardiac output. Besides, it is revealed that KP-102 is desirable from a clinical viewpoint since it has no effects on the heart rate, the mean blood pressure and the double product as an index of myocardial oxygen consumption.

INDUSTRIAL APPLICABILITY

Pralmorelin exhibited a marked positive inotropic activity and increased cardiac output as compared to the other growth hormone secretagogues. Hence, based upon this cardiotonic action, the pralmorelin containing preparations of the present invention are useful as preparations for preventing or treating acute heart failure, chronic heart failure at a phase of acute exacerbation or heart failure at a phase of transition to chronic heart failure.

Aside from having cardiotonic action, pralmorelin has no effect on the heart rate, nor does it cause any side effects such as hypotension. Therefore, unlike the conventional drugs for acute heart failure, the pralmorelin containing preparations of the invention can also be applied to hypotensive patients.

What is claimed is:

1. A method of treating acute heart failure, chronic heart failure at a phase of acute exacerbation or heart failure at a phase of transition to chronic heart failure, which comprises administering to a patient in need thereof D-alanyl-3-(naphthalen-2-yl)-D-alanyl-L-alanyl-L-tryptophyl-D-phenylalanyl-L-lysinamide and/or a salt thereof.

2. The method of claim 1, wherein said D-alanyl-3-(naphthalen-2-yl)-D-alanyl-L-alanyl-L-tryptophyl-D-phenylalanyl-L-lysinamide and/or a salt thereof is an acid addition salt of D-alanyl-3-(naphthalen-2-yl)-D-alanyl-L-alanyl-L-tryptophyl-D-phenylalanyl-L-lysinamide.

3. The method of claim 2, wherein said acid addition salt of D-alanyl-3-(naphthalen-2-yl)-D-alanyl-L-alanyl-L-tryptophyl-D-phenylalanyl-L-lysinamide is D-alanyl-3-(naphthalen-2-yl)-D-alanyl-L-alanyl-L-tryptophyl-D-phenylalanyl-L-lysinamide dihydrochloride.

4. The method of claim 1, wherein said heart failure is acute heart failure.

5. The method of claim 1, wherein said heart failure is chronic heart failure at a phase of acute exacerbation.

6. The method of claim 1, wherein said heart failure is at a phase of transition to chronic heart failure.

7. The method of claim 2, wherein said heart failure is acute heart failure.

8. The method of claim 2, wherein said heart failure is chronic heart failure at a phase of acute exacerbation.

9. The method of claim 2, wherein said heart failure is at a phase of transition to chronic heart failure.

10. The method of claim 3, wherein said heart failure is acute heart failure.

11. The method of claim 3, wherein said heart failure is chronic heart failure at a phase of acute exacerbation.

12. The method of claim 3, wherein said heart failure is at a phase of transition to chronic heart failure.

* * * * *